United States Patent
Zheng et al.

(10) Patent No.: US 7,597,104 B2
(45) Date of Patent: Oct. 6, 2009

(54) METHOD AND DEVICE FOR IMMOBILIZATION OF THE HUMAN BREAST IN A PRONE POSITION FOR RADIOTHERAPY

(76) Inventors: Mike Q. Zheng, 6417 Mellow Wine Way, Columbia, MD (US) 21044; Ying Su Yu, 12707 Chapel Chase, Clarksville, MD (US) 21029

( * ) Notice: Subject to any disclaimer, the term of this patent is extended or adjusted under 35 U.S.C. 154(b) by 168 days.

(21) Appl. No.: 11/726,961

(22) Filed: Mar. 23, 2007

(65) Prior Publication Data

US 2008/0230074 A1   Sep. 25, 2008

(51) Int. Cl.
  *A61B 19/00*  (2006.01)
  *A61B 5/05*  (2006.01)
  *A61B 6/04*  (2006.01)
  *A47B 13/00*  (2006.01)
  *A47C 17/86*  (2006.01)

(52) U.S. Cl. ............... 128/869; 600/415; 606/130; 378/37; 5/601; 5/630

(58) Field of Classification Search ......... 606/130, 606/13; 600/436, 427, 437, 428, 407, 562, 600/415; 128/874, 875, 876, 882, 869; 604/75; 2/67; 450/38, 37, 55; 5/643, 630, 632, 601, 5/621, 910; 378/37, 208, 204
See application file for complete search history.

(56) References Cited

U.S. PATENT DOCUMENTS

| | | | | |
|---|---|---|---|---|
| 2,579,365 A | * | 12/1951 | Conde | ........................ 450/39 |
| 5,308,321 A | * | 5/1994 | Castro | ........................ 600/415 |
| 5,437,280 A | * | 8/1995 | Hussman | ..................... 600/417 |
| 5,569,266 A | * | 10/1996 | Siczek | ........................ 606/130 |
| 6,011,987 A | * | 1/2000 | Barnett | ........................ 600/414 |
| 6,419,680 B1 | * | 7/2002 | Cosman et al. | ............. 606/130 |
| 6,440,100 B1 | * | 8/2002 | Prentiss | ....................... 604/74 |
| 2004/0073106 A1 | * | 4/2004 | Lee et al. | .................... 600/415 |

* cited by examiner

*Primary Examiner*—Patricia Bianco
*Assistant Examiner*—Ophelia Hawthorne
(74) *Attorney, Agent, or Firm*—Ober/Kaler; Royal W. Craig (57) ABSTRACT

A system and method for immobilization of the human breast in a prone position during imaging and radiotherapy. The system includes a vacuum-assisted breast immobilization cup comprising two layers joined together with an air space between. The inner layer has densely perforated holes while the outer layer is airtight. When a negative vacuum is applied to the intermediate airspace the breast tissue is sucked against the mesh wall of the inner layer to preventing sliding. In addition, the cup assembly is locked into a fixed position against the patient torso via a body fixture, as well as against the patient support structure. The established geometric relationship among the cup, chest wall, imaging/treatment table or couch may be accurately repeated. The system further includes a three-dimensional localization system to uniquely place the breast in a coordinate system having fixed geometric relationship with the breast immobilization cup.

19 Claims, 10 Drawing Sheets

METHOD AND DEVICE FOR IMMOBILIZATION OF THE HUMAN BREAST IN A PRONE POSITION FOR RADIOTHERAPY

BACKGROUND OF THE INVENTION (1) Field of the Invention

The present invention generally relates to radiotherapy equipment and, more particularly, to a method and system for breast tissue immobilization for breast imaging and therapy.

(2) Description of Prior Art

Breast cancer is the most prevalent malignancy among women. Close to 211,000 cases of breast cancer were diagnosed in the United States in 2006 (Cancer Facts & Figures, 2006, American Cancer Society). The lifetime risk of any particular woman in North America getting breast cancer is about 1 in 7.

On a more promising note, breast cancer awareness and screening have resulted in the majority of breast cancers being diagnosed in the early-stage of the disease. The current standard of treatment for most early stage breast cancers is breast conservation therapy (BCT), consisting of lumpectomy followed by 6-8 weeks of radiation therapy, mostly irradiating the whole breast. Although the outcome of BCT is very favorable, the invasive surgical procedure and the lengthy radiation treatment significantly worsen the quality of life for such a large population of patients.

After years of clinical trial and studies, there are convincing arguments that the benefit of standard treatment of irradiating the breast following the lumpectomy is the sterilization effects of radiation on the micro extension of the tumor around the surgical bed (Morrow et al., J Natl Cancer Inst, 1995; 87:1669-73). This is the main hypothesis of the current push of accelerated partial breast irradiation (APBI). Instead of irradiating the entire breast, radiation is delivered to a segment around the lumpectomy cavity. With increased daily dose, the radiation treatment time is reduced from seven or eight weeks to four or five days, which could potentially impact the lives of thousands of cancer patients in a positive way.

Currently there are five Phase III clinical trials comparing APBI with whole breast irradiation. In the US, NSABP's B39 trial and RTOG's 0413 trial are ongoing (Arthur et al., J. of Clinical Oncology, 2005; 23:1726-35). This trial alone is targeted to enroll 3000 patients. Some early institutional study results are emerging, with 5 year reoccurrence rate ranging from 1-4% (Neihoff et al., Radiother Oncol 2006; 79:316-20; Chen et al., Cancer 2006; 106:991-9; Zannis et al., Am J Surg 2005; 190:530-8).

When irradiating breast, patient position is an emerging concern. Most radiation treatments are in supine position, while the most sensitive and specific MRI imaging are in prone position. Realizing the limitation of the supine position, a suggestion of treating patients with large breasts in a prone position was proposed by Merchant et al., (Int. J Radiat Oncol Biol Phys., 1994; 30:197-203). They found that, for large-breasted women treated in the prone position, the size of the high-dose region at the base of the breast was reduced. The tissue volume of normal lung and the heart included in the treatment fields was also decreased. Stepaniak et al., (Int. J. Rad Onc Biol Phys 2005; 63:S532-3) reported that analyses based on the 4D CT datasets from 3 patients showed that the average intra-treatment chest wall movement was less than 1 mm.

Another benefit of breast radiation treatment in the prone position is that it can reduce the motion resulting from cardiac systole and respiratory movement.

As concluded, prone position breast irradiation appears to be a simple and effective alternative to irradiation of the breast in the conventional supine position when the supine position is likely to result in unacceptable dose in homogeneity or significant doses to normal tissues.

When only irradiating the surgical bed locally, it is very important to treat the breast with precise geometric accuracy. Modern imaging technologies such as Computed Tomography (CT), Magnetic Resonance Imaging (MRI), and Positron Emission Tomography (PET), can assist tumor localization with high geometrical accuracy. However, due to the pliable nature of breast tissue, it is a challenge to maintain the geometry unchanged during the entire process of imaging, treatment planning, and multi-fractional treatment delivery.

A number of breast tissue immobilization devices have been developed in the past. The most widely used procedure is that used in mammogram which uses two parallel plates to compress the breast tissue. Other methods were developed to meet different purposes, such as a compression-based device (Kaiser et al., J Magn Reson Imaging 1995; 5:525-8; Meyer et al., Radiology 1988; 169:266; Mark G. Fontenot, U.S. Pat. No. 6,589,254 Jul. 8, 2003; Bulkes et al., US publication 20050228267 Oct. 13, 2005), thermoplastic mask (Kaiser et al., J Magn Reson Imaging 1995; 5:525-8; Zeggelink et al., Medical Physics 2002; 29:2062-69), and contour cushions (Frederick N. Mellinger, U.S. Pat. No. 3,934,593 Jan. 27, 1976).

In U.S. Pat. No. 6,146,377, Lee et al. designed a breast-shaped device for biopsy and other invasive medical procedures. This device has a two-member structure to facilitate suction-induced breast stabilization/immobilization and has multiple openings to perform medical procedures in nipple/areola complex and other part of the breast.

Rioux et al. in US publication 2004/0215101 disclosed a two-layer device which has a medical device holder, open section for medical procedures, and vacuum/suction enabled breast immobilization mechanism. However, these existing methods and devices lack key features for effective APBI treatment: (a) immobilization must be precise, reliable, repeatable, and predictable; (b) applicable for prone position; (c) includes a mechanism to interlock the immobilizing device with the imaging couch or treatment bed; (d) be capable of reproducing the geometry when recurring procedure is needed; (e) have a stereotactic imaging registration mechanism for precise treatment setup; and (f) depress the untreated breast to minimize unnecessary radiation exposure. It is, therefore, an objective of current invention to address these needs.

SUMMARY OF THE INVENTION

It is therefore the primary object of the present invention to provide a method and system for breast tissue immobilization during breast imaging and therapy that maintains a precise geometric relationship among the breast, chest wall, imaging and treatment table or the couch.

It is another object to provide a method and system for breast tissue immobilization as described above that provides an immobilization that is precise, reliable, repeatable, and predictable.

It is another object to provide a method and system for breast tissue immobilization as described above that facilitates imaging and therapy with the patient in a prone position.

It is another object to provide a method and system for breast tissue immobilization as described above that includes a mechanism to interlock the immobilizing device with an imaging couch or treatment bed.

It is another object to provide a method and system for breast tissue immobilization that is capable of reproducing a positioning geometry when a recurring procedure is needed.

It is still another object to provide a method and system for breast tissue immobilization that includes a mechanism to correlate the imaging slice position to the physical position of the immobilization device.

It is still another object to provide a method and system for breast tissue immobilization that depresses the untreated breast to minimize unnecessary radiation exposure.

In accordance with the foregoing and other objects, the present invention is a system and method for immobilization of the human breast in a prone position for radiotherapy. The system includes a breast immobilization cup equipped with a vacuum source assembly. The breast conforms to the cup's inner surface shape when the vacuum is applied. The wall of the cup comprises two layers joined together. The inner layer comprises a mesh of densely perforated holes and the outer layer is solid and airtight. There is a space between the two layers. By applying negative pressure to the space between the two layers through a vacuum conduit, the breast tissue is sucked against the mesh wall of the inner cup preventing sliding movement between the skin of the breast and the cup's inner surface. The negative pressure also helps pull the breast tissue away from the chest wall (if a tumor is close to the chest wall, such downward shift makes it more accessible for the radiation beam to target). The negative pressure in between the two layers is preferably monitored and kept constant.

The cup assembly has a rigid rim, which serves several purposes. First, it firmly holds a number of locking pins, which engage with a locking mechanism on the imaging couch, breast coil, treatment bed, or other positioning device. A snug fitting results in a precisely-fixed geometric relation between the cup assembly and these medical devices. Second, to further restrain breast tissue from deforming due to body movement, the rim is secured to the torso through a body fixture which comprises a solid frame to hold the rim and a torso-encircling wrap. The rim may also be used to house other functional structures such as vacuum conduit(s), imaging registration stripes, etc.

When the patient is set up in prone position, the breast tissue tends to fall away from the chest wall, making it easier to spare the chest wall and organs in the thorax. With the negative pressure, there will be additional mild pulling of the breast tissue away from the chest wall for easy targeting.

The locking pins (which engage with the locking mechanism on the imaging couch) also pass through pin holes in the body fixture. Thus, when the fastening belts are tightened, the cup and body fixture is restrained to the torso, and the protruding pins can be fit into corresponding indentation holes spaced around the opening on the imaging table or the treatment couch. The breast drops through the table/couch. The pins may be locked down once the patient is set on the imaging table or the treatment couch, with the cup passing through an opening on the couch. The locking pins can be released by a releasing mechanism. Both the imaging couch and the treatment bed need to have matching locking mechanism.

After the patient has completed imaging scans such as CT, NMR, or PET, the phase of treatment planning and treatment delivery begins. The immobilizing device may need to be taken off and put back on when treatment lasts more than one day or prolonged suction is undesirable under certain medical conditions. It is important that when the device is put back on, the established geometric relationship among the breast, cup, chest wall, imaging and treatment table or the couch is accurately restored. With the locking pin mechanism in place, the main concern resides in whether the breast can be positioned in the cup exactly as before. To address this concern, a skin marking system for registering skin position (in relation to immobilizing device) is provided. The cup is preferably made of transparent material with finely printed marking lines on its inner layer 7. Each of the marking lines is uniquely labeled and structured so that any point on the inner layer of the cup has a set of unique coordinates. Before the vacuum cup is put on the first time, a number of skin markers are made on the skin of the being treated breast. The skin markers remain visible through the transparent cup during the entire treatment period and can be marked in the places which coordinates can be easily seen and recorded when the cup is put on. These recorded coordinates can be used as guidance for following setups to maintain setup accuracy.

To further facilitate the skin marker matching procedure, an alternative embodiment is disclosed that incorporates a multiple vacuum band structure. During the repeated setup, the vacuum of these bands can be individually applied or released by control valves. This will allow the breast to be partially immobilized in one band while position adjustment can be performed in the non-immobilized band(s) to reach ultimate repositioning accuracy.

Most modern imaging modalities such as CT, MRI, and PET use "slice numbers", each with an internal Z-coordinate. Such internal coordinate system is not fixed with any anatomical landmarks. The same anatomical landmark will have different coordinates in different imaging sessions. In the present context, it is important to know where that center is in regard to the cup. This is accomplished by imaging registration stripes integrated into the cup. One imaging stripe provides a scale running radially around the base of the cup, and the other provides a scale running from point-to-diametric-point overtop the cup. This way, for every image slice, the imaging registration stripes can be used to provide three coordinates to register the cup position unequivocally.

The present system and device for breast tissue immobilization is precise, reliable, repeatable, and predictable, and facilitates imaging and therapy with the patient in a prone position, as well as complete reproduction of that positioning geometry when a recurring procedure is needed. Moreover, the untreated breast is depressed to minimize unnecessary radiation exposure.

BRIEF DESCRIPTION OF THE DRAWINGS

Other objects, features, and advantages of the present invention will become more apparent from the following detailed description of the preferred embodiments and certain modifications thereof when taken together with the accompanying drawings in which.

DETAILED DESCRIPTION OF THE PREFERRED EMBODIMENTS

The present invention is a method and system for breast tissue immobilization during breast imaging and therapy that maintains a precise geometric relationship among the breast, chest wall, imaging and treatment table or the couch.

Figure 1:
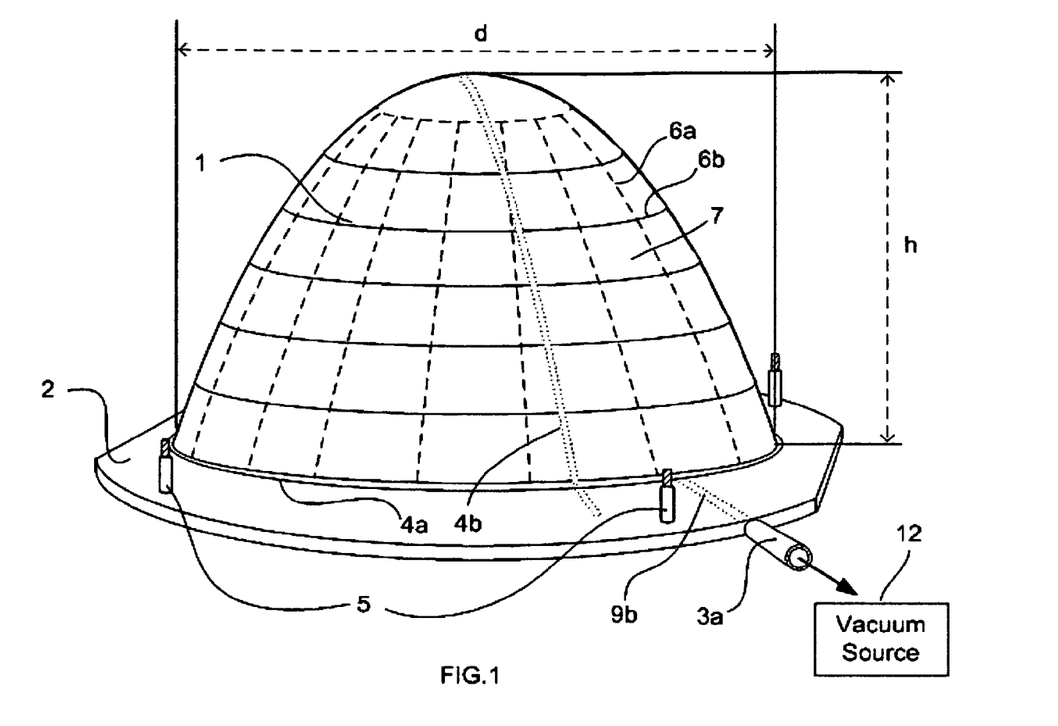
FIG. 1 is a perspective view of a breast immobilization system according to a first embodiment of the present invention.

FIG. 1 is a perspective view of a breast immobilization system according to a first embodiment of the present invention.

Figure 2:
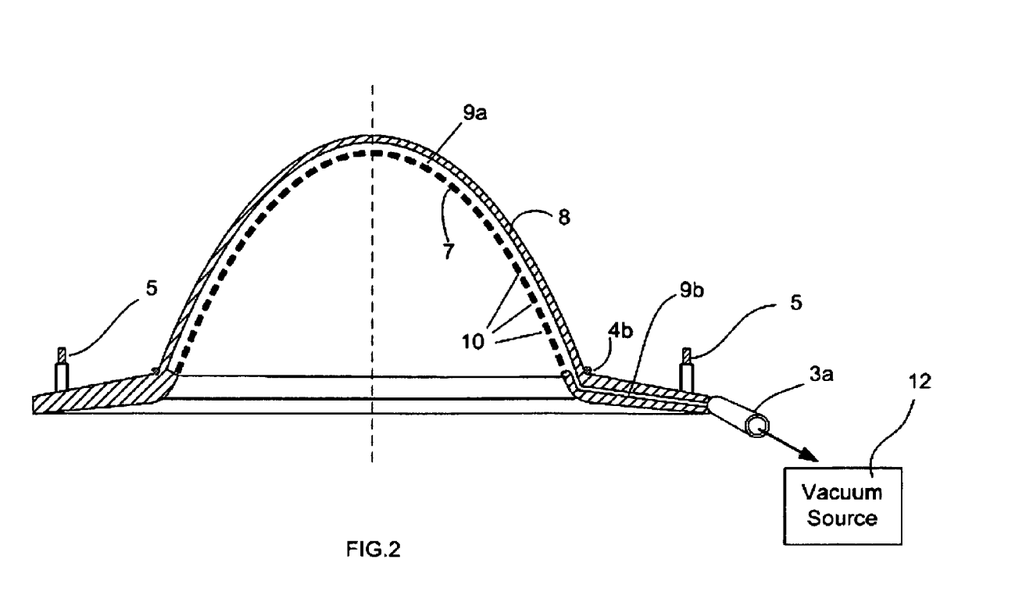
FIG. 2 is a side cross-section of the breast immobilization system of FIG. 1.

FIG. 2 is a side cross-section of the breast immobilization system of FIG. 1.

With combined reference to FIGS. 1-2, the system includes a breast immobilization cup assembly 1 pneumatically connected to a vacuum source 12. As best seen in FIG. 2, the wall of the cup assembly 1 comprises two layers joined together, both being generally concave (such as parabolic as shown) for receiving a human breast. The inner layer 7 comprises a concave hard shell formed with densely perforated holes 10. The outer layer 8 is a slightly larger concave hard shell that is solid and airtight. The inner layer 7 fits within the outer layer 8 but leaves a slight airspace between the two layers 7, 8. A vacuum conduit 3 is attached by conventional tubing to the vacuum source 12 and conveys a vacuum there from into the airspace between the two layers 7, 8. In the illustrated embodiment, the outer layer 8 is formed with a flange 2 that serves multiple purposes: providing a means for mounting and positioning the cup assembly 1 (as will be described), plus an inner shelf for securing the inner layer 7 inside the outer layer 8. In addition, the vacuum conduit 3 propagates through an interior channel formed in the flange 2 into the airspace.

In operation, the breast tissue is pulled outward from the chest and is pulled against the cup assembly's inner layer 7 when a negative vacuum is applied by vacuum source 12. By applying negative pressure to the airspace between the two layers 7,8 through the vacuum conduit 3, the breast tissue is sucked against the mesh wall of the inner cup, thereby preventing sliding movement between the skin of the breast and the cup assembly's inner layer 7. The negative pressure in between the two layers is preferably monitored and kept constant, and this is easily accomplished via pressure gauges supplied with the vacuum source 12. To achieve the maximum accuracy, repeatability, and patient comfort level, a stable and well controllable vacuum source is important. Preferably, the vacuum source 12 should have the following features: 1) it should be portable since stable and uninterrupted vacuum is needed during patient imaging, transporting, waiting, and treatment; (b) Made of MRI compatible material to be used in MRI room; (c) built-in redundancy to prevent system failure and vacuum drop; (e) and have integral vacuum level adjusting and alarm system for consistency and safety concerns.

Figure 3:
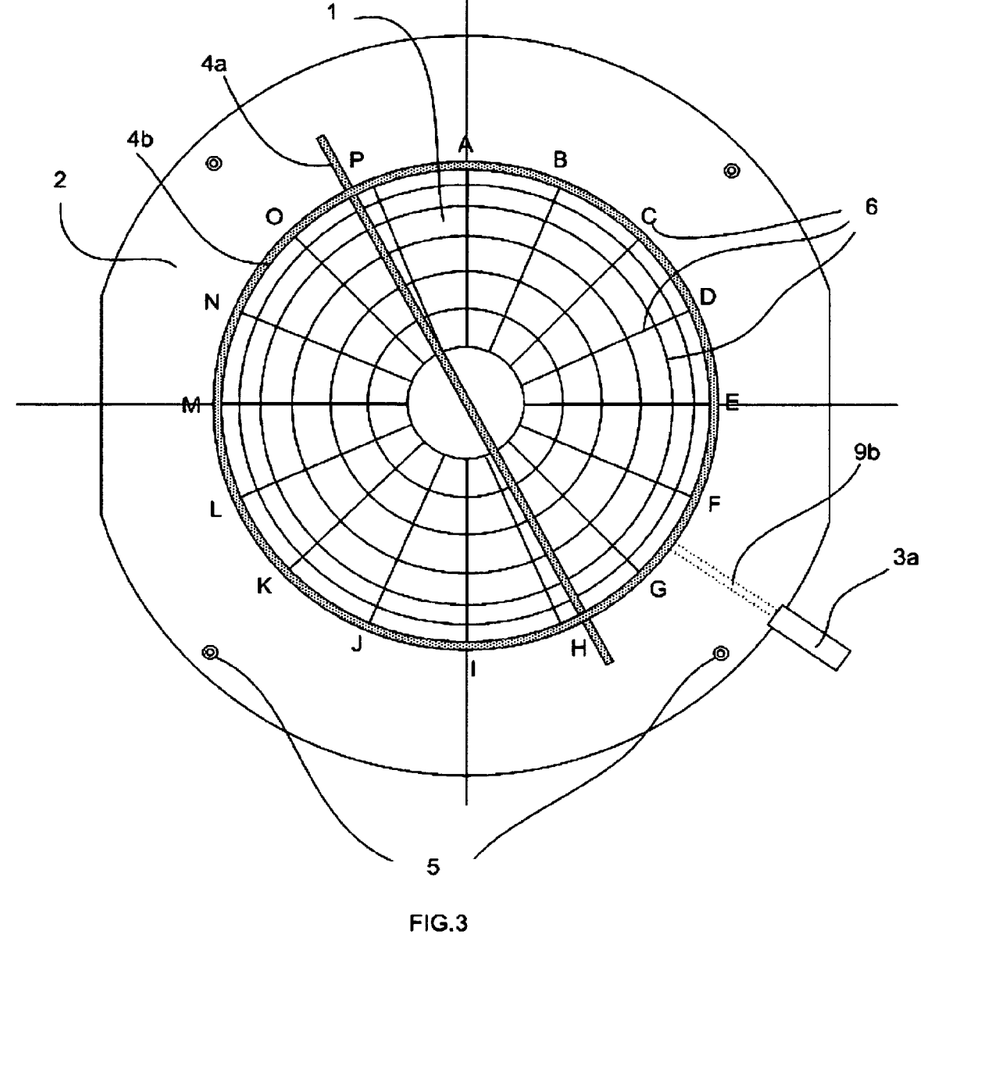
FIG. 3 is a top view of the device illustrating radial stripes 6b and axial stripes 6a, as well as the imaging registration stripes 4a (radial sightline) and 4b (axial sightline).

The flange 2 of the cup assembly 1 is a rigid annular rim that may be integrally formed with the outer layer 8. The flange 2 is equipped with a plurality of coaxially-oriented radially-spaced locking pins 5. The locking pins 5 protrude forwardly (with the cup) as shown in FIGS. 2-3) to engage a body fixture on the patient. The body fixture comprises a torso-encircling vest or wrap equipped with another breast frame (described below). The breast frame encircles the breasts while providing apertures, and thereby holds the cup against the chest. Specifically, the cup assembly 1 nests within the body fixture (sandwiched thereby against the patient), the flange 2 being held captive under the breast frame and with the pins 5 passing through corresponding holes in the breast frame to fix the position of the cup assembly 1 relative to the body fixture.

The pins 5 continue through the breast frame of the body fixture and lock into the patient support structure.

The flange 2 may also be used to anchor and/or house other functional structures such as vacuum conduit(s), imaging registration stripes, etc.

Considering that the above-described immobilization device will most likely be used in CT and MRI scans, all the material used to make the cup assembly, including, but not limited to, the cup, the rim, locking pins, body fixture, breast depressor, etc., should be made of MRI compatible metal or nonmetallic material.

The present system is especially suited for use in conjunction with an imaging couch, treatment bed or other support structure on which the patient rests in a prone position (lying face down). When the patient rests in a prone position, the breast tissue tends to fall away from the chest wall, making it easier to image the breasts without exposing the chest wall and organs in the thorax. With the negative pressure of the present invention, there is an additional mild pulling of the breast tissue away from the chest wall for even easier targeting.

In use, the cup assembly 1 is placed on the patient's breast, followed by the application of vacuum. After desired positioning is achieved, the cup assembly is wrapped in the body fixture (torso-encircling vest or wrap with solid breast frame). The body fixture is donned and tightened. The patient is then placed on the support structure with pins 5 fit into corresponding locking holes on the support structure (table, imaging couch, etc.).

The locking pins 5 must obviously be releasable, and any of a variety of tight-fit, pin-lock configurations will suffice such as known ball locking pins, or releasable detent pins.

Once lying on the support structure with cup assembly 1 firmly locked through the body fixture and into the support structure, it is possible to complete a variety of imaging scans such as CT, NMR, or PET. After the patient has completed the imaging scans the immobilizing system may need to be taken off and put back on (sometimes treatment lasts more than one day, or prolonged suction is undesirable under certain medical conditions). In this case it is important to note that when the device is put back on, the established geometric relationship among the breast, cup, chest wall, imaging and treatment table or the couch needs to be accurately restored. With the locking pins 5 in place, the main concern resides in whether the breast can be positioned in the cup exactly as before. To address this concern, a skin marking system is contemplated.

To implement the skin marking system, the outer layer 8 of the cup assembly 1 is preferably formed from transparent material (plastic) and the inner layer 7 is likewise transparent. The inner layer 7 is demarcated with finely printed or etched marking lines on its inner surface that are visible from outside. For example, FIG. 1 shows a grid work of axial stripes 6a and radial stripes 6b. Before the vacuum cup assembly 1 is put on for the first time, a number of skin markings are made on the skin of the breast. The skin markers remain visible through both layers 7, 8 of the transparent cup assembly 1 during the entire treatment period and are preferably made in areas that register along the coordinates of the inner layer 7, so that they can be easily seen and recorded when the cup assembly 1 is put on.

The height (h) and the diameter of the cup (d) can vary to fit different sizes of breast while keeping the geometry of the locking pins 5 unchanged.

FIG. 3 is a top view of the device illustrating the radial stripes 6b and axial stripes 6a. Each of these marking lines 6a, 6b is uniquely labeled and structured as shown so that any point on the inner layer 7 of the cup assembly 1 has a set of unique coordinates. These recorded coordinates can be used as guidance to maintain setup accuracy.

The present invention contemplates an image slice registration system as shown in FIG. 1 for correlating the digital position of the images (CT or MRI) to the physical position of the cup assembly 1. The image registration system here comprises two stripes 4a and 4b made of imaging-opaque materials to distinguish them from the image. The stripes 4a and 4b are integrated into the outer layer 8 and include an axial sightline 4b that continues over the dome, and a radial sightline 4a encircling the base of the dome.

Again, FIG. 3 is a top view of the device illustrating the axial sightline 4b and radial sightline 4a. Using this image slice registration system, any given position (e.g., the center of a cancer) may be located in a given slice with regard to the cup. This is accomplished by integrating imaging stripes into the cup assembly 1. Specifically, for every image slice, the imaging stripes 4a, 4b can be used to provide three coordinates (described in more detail below in regard to FIG. 8) to register the cup position unequivocally. A lookup-chart can be used to calculate the spatial transfer.

Figure 4:
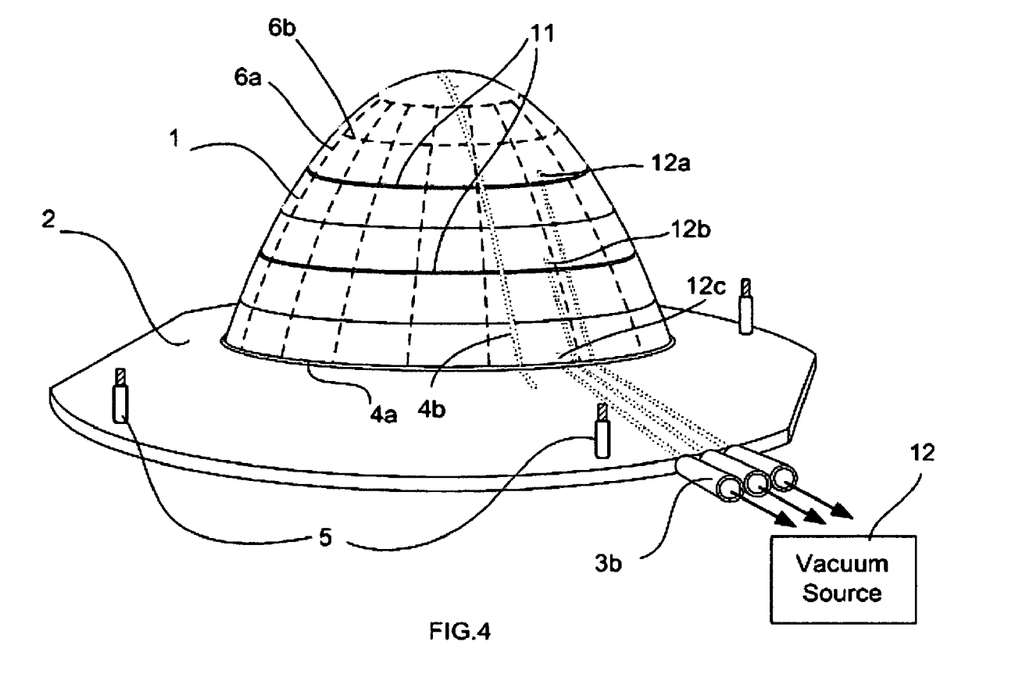
FIG. 4 is a perspective view of an alternative embodiment of a breast immobilization system according to a second embodiment of the present invention with a multiple vacuum band structure.

FIG. 4 is a perspective view of an alternative embodiment of a breast immobilization system according to a first embodiment of the present invention with a multiple vacuum band structure that further facilitates the above-described skin marker matching procedure.

Figure 5:
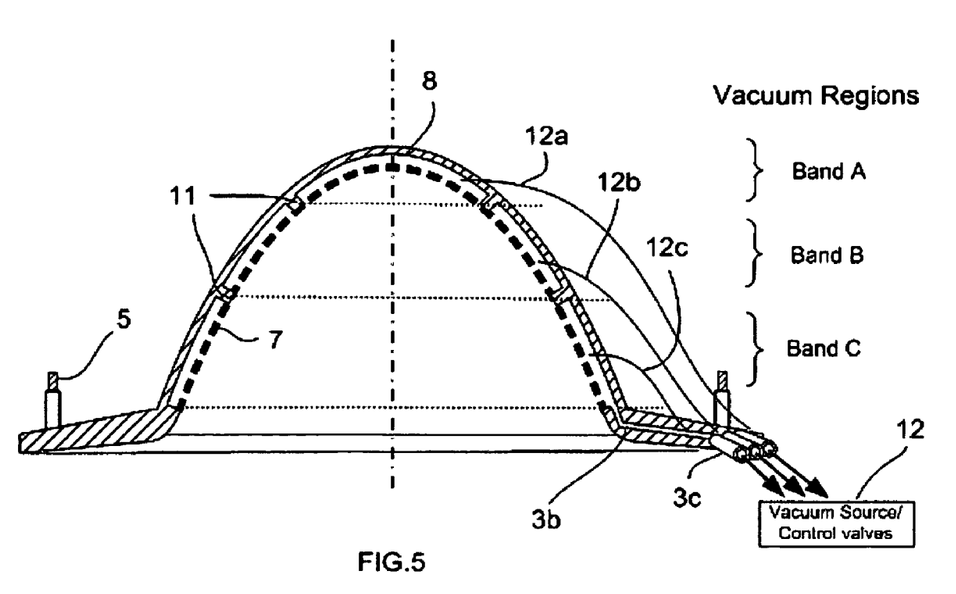
FIG. 5 is a side cross-section of the embodiment of FIG. 4.

FIG. 5 is a side cross-section of the embodiment of FIG. 4.

With combined reference to FIGS. 4-5, the system is similar to that of FIGS. 1-2 with cup assembly 11 pneumatically connected to a vacuum source 12. However, as best seen in FIG. 4, the outer layer 8 of the cup assembly 1 includes a plurality of radial ribs 11 that form partitions against the inner layer 7. The inner layer 7 again fits within the outer layer 8 but leaves a plurality of distinct airspaces between the two layers 7, 8, here three being shown and designated band A, band B, band C. A corresponding number of vacuum conduits 3A-C are attached by discrete tubes to the vacuum source 12 and convey three distinct vacuum pressures into the partitioned airspaces of band A-C between the two layers 7, 8. The flange 2, while otherwise the same, propagates the three vacuum conduits 3A-C separately through distinct interior channels formed through the flange 2 into the airspaces.

During setup, the vacuum to the distinct bands A-C can be individually applied or released by control valves at the vacuum source 12. This added functionality allows the breast to be partially immobilized in one band while position adjustments can be performed in the non-immobilized band(s) to reach the ultimately desired repositioning accuracy.

Given either of the foregoing embodiments, while one breast is being treated, exposure of the other breast should be minimized, and this is easily accomplished by affixing a breast suppression cup assembly over the untreated breast.

Figure 6:
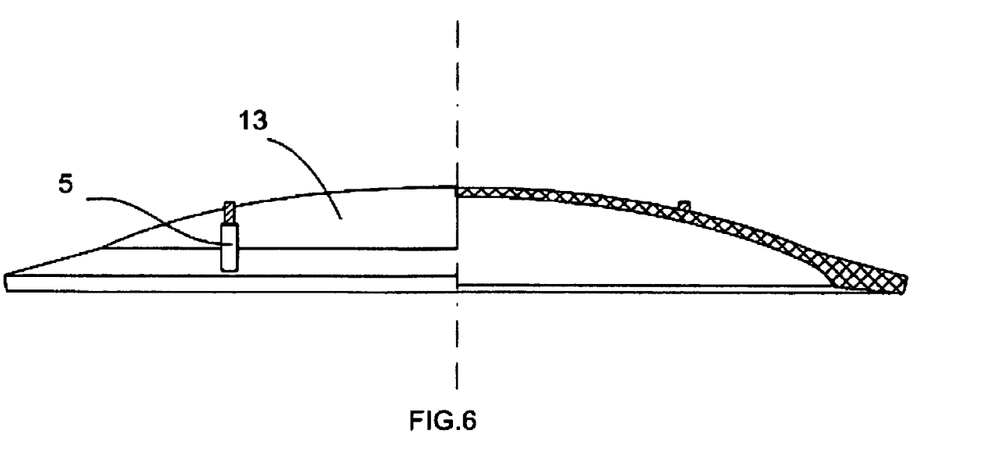
FIG. 6 is an example of a breast depressing cup assembly for confining and flattening the untreated breast.

FIG. 6 is an example of a breast suppression cup assembly 21 which generally comprises the same flange 2 and pins 5 as described above, but a flattened convex breast suppression plate 13 for confining and flattening the untreated breast. When in prone position, the pendulous untreated breast would otherwise be needlessly exposed to radiation and could complicate the treatment setup. The almost-flat, slightly cone-shaped breast depressor plate 13 compresses the untreated breast against the chest wall to facilitate the treatment as well as to reduce its unnecessary exposure to the radiation. To improve the patient comfort level and air sealing, the skin side of the plate 13 may have a layer of elastic gel-like material.

Figure 7:
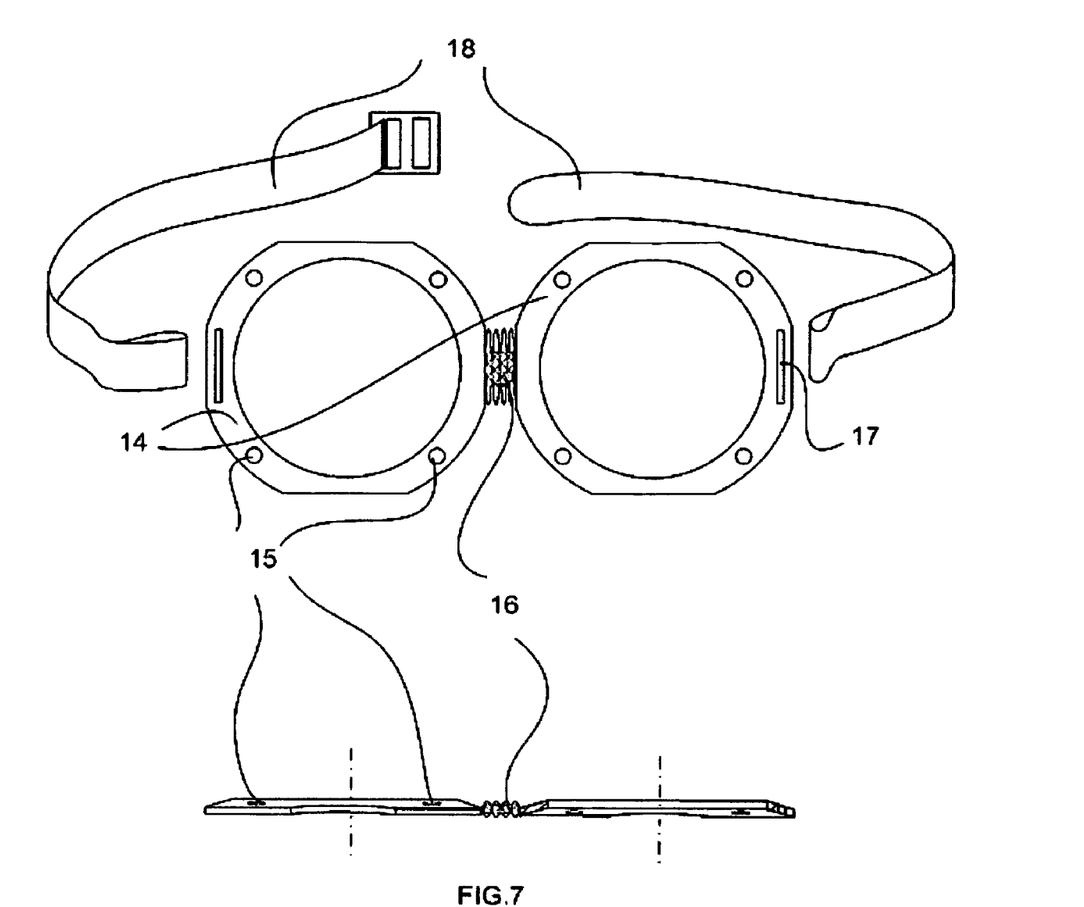
FIG. 7 is an exploded frontal diagram of an exemplary embodiment of the patient body fixture.

FIG. 7 is an exploded frontal diagram of an exemplary embodiment of the patient body fixture, with inset side view. The patient body fixture here comprises a pair of torso-encircling straps 18 attached to adjoining solid breast frames 14. The frames 14 are connected by a resilient connector 16, and each frame 14 is defined by a central aperture that encircles one breast while allowing it to protrude into the cup assemblies 1. Each frame is also equipped with radially-spaced registration holes 15 for insertion of the pins 5 of the cup assembly 1. The pins 5 fit into corresponding holes in the frames 14 and lock therein to secure the cup assemblies 1 to the body fixture, thereby establishing the requisite fixed geometric relation between the breasts and cup assembly 1. The straps 18 of the body fixture are anchored to the sides of the opposing frames 14 as shown, and one strap 18 includes a buckle for attachment around the torso.

Figure 8:
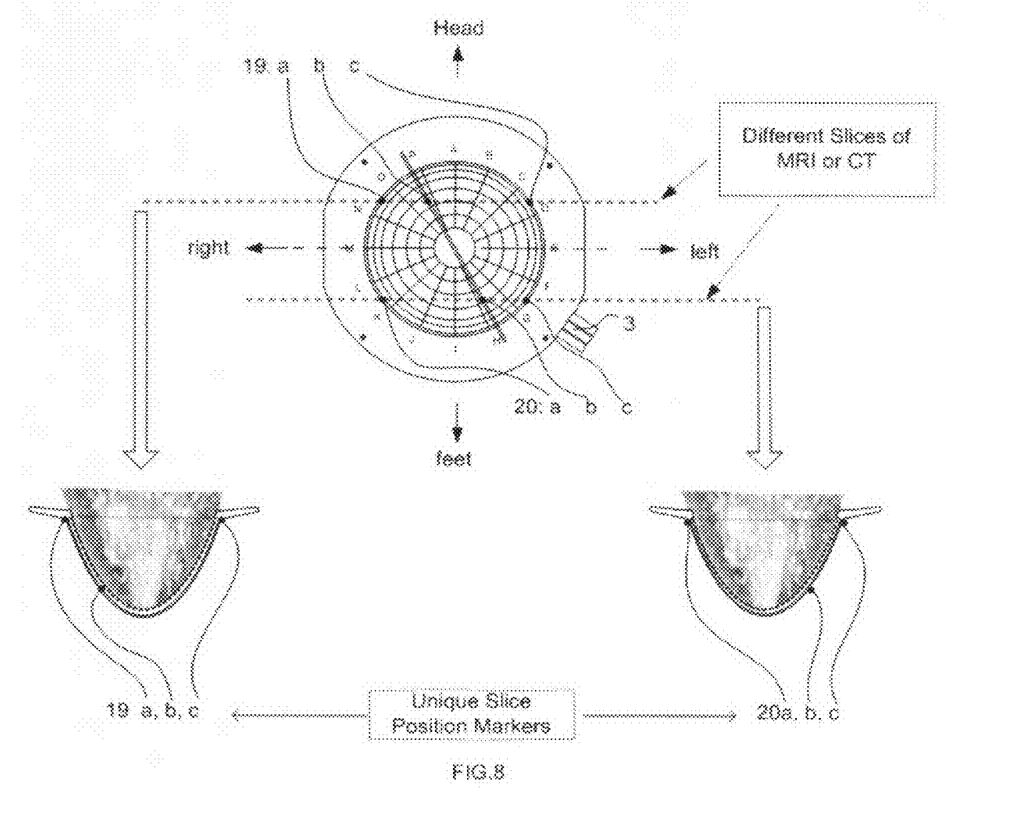
FIG. 8 is an illustration of how the imaging slice registering system works.

FIG. 8 is an illustration of how the above-described imaging registration system works to achieve three-dimensional localization. Modern imaging modalities, such as CT, MRI, can provide 3-dimensional images of body structure with precision in the range of millimeters to sub-millimeters. These images are the basis for tumor localization, treatment planning, and subsequent radiation therapy. A correlative reference system is needed to link the digital form of structural information such as GTV (Gross Tumor Volume), PTV (Primary Tumor Volume), isocenter, Z-coordinates, etc., to the physical geometry of the cup assembly 1. These relationships, once established, can be extended further to other support structure which the cup assembly is fixed to, such as the treatment bed, imaging table, etc. Therefore, a stereotactic imaging registering system is designed by integrating a number of geometric markers, in the shape of stripes, consisting of high imaging contrasting material, liquid or solid, into the cup assembly 1. Since these markers have unique spatial coordinates in relation to the breast cup assembly 1, these markers can be accurately localized in CT and/or MRI images, and a relationship between imaging coordinates and cup geometry can be established.

Figure 9:
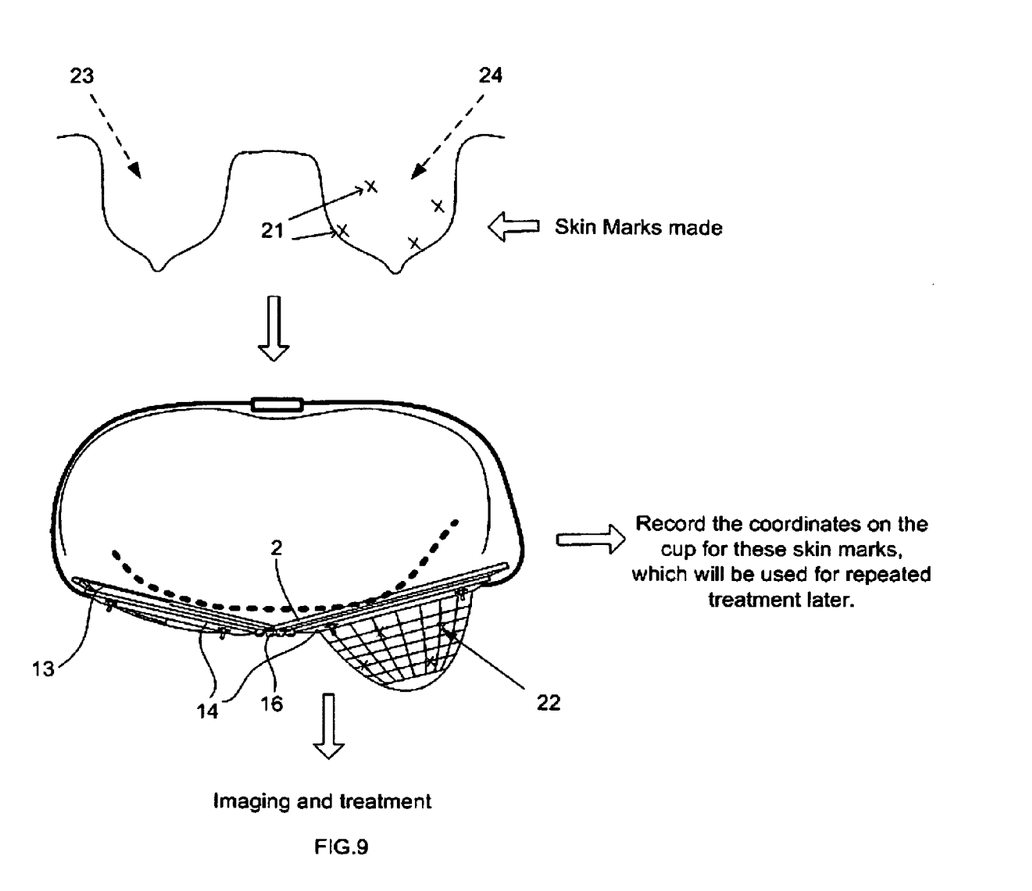
FIG. 9 is an illustration of how the skin marking system works.

As illustrated in FIG. 8, taking image slice 19 as an example, its intersection to stripe 4a (dots 19a and 19c) and stripe 4b (dot 19b) has different geometrical position from that in any other image slices (such as that in slice 20). Therefore, for any image slice, based upon the location of the three intersection dots in its image, its physical location to the cup assembly can be established FIG. 9 is an illustration of how the skin marking system works. 23 is untreated breast and 24 is the treated breast. Before the cup assembly is put on the first time, a number of semi-permanent skin marks (21) are made on the treated breast (24). After the cup assembly is put on, and desired vacuum level and positioning are achieved, each skin mark's corresponding coordinate to that finely printed in the inner layer 7 can be recorded though the transparent layers 7 and 8. These recorded coordinates (22) can be used as guidance for repeated treatment later.

Figure 10:
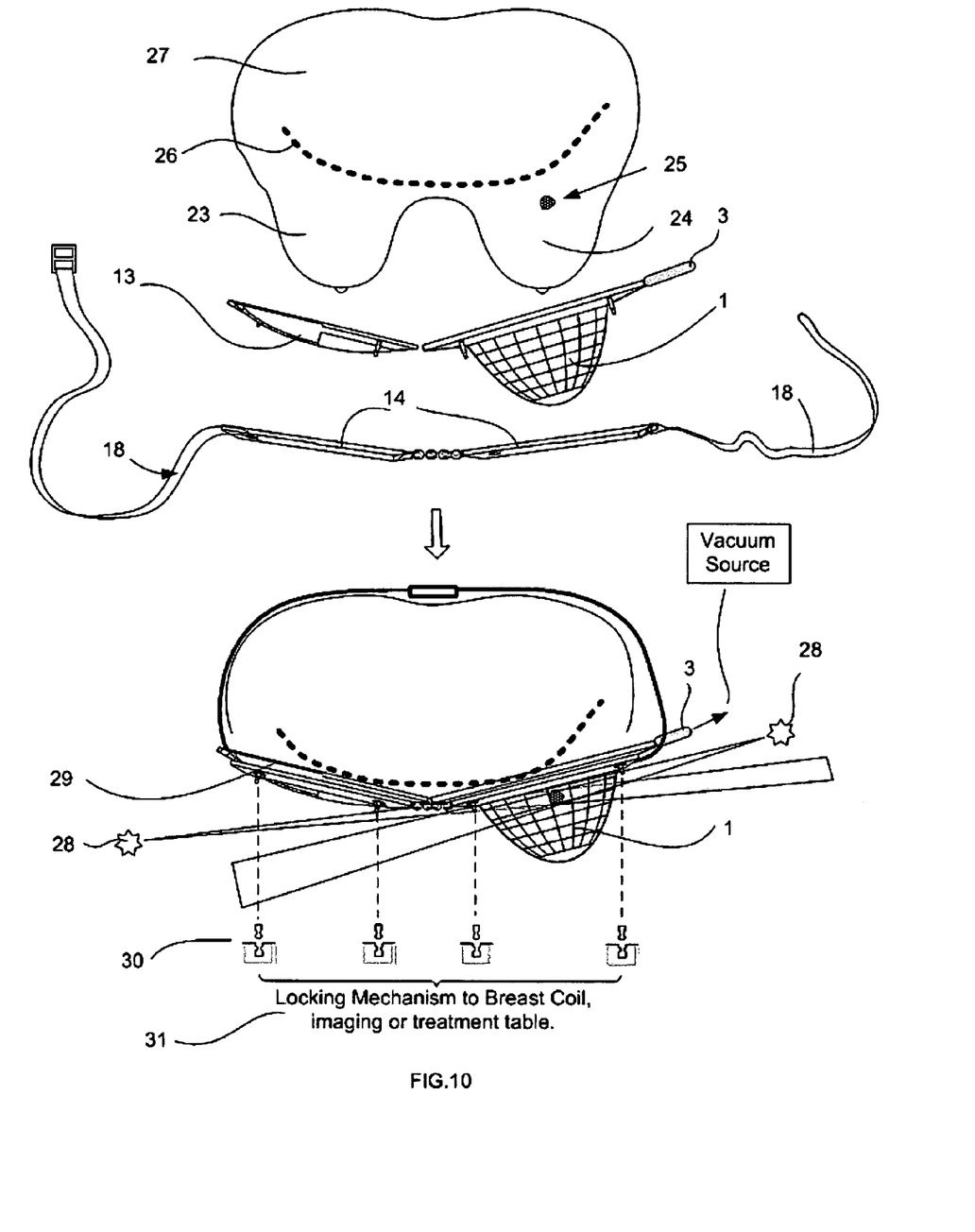
FIG. 10 is an illustration of the method of using a breast immobilization system.

FIG. 10 is a general illustration of the use of the system for breast tissue immobilization during breast imaging and therapy. The chest wall 27 is shown along with the treated (24) and untreated (23) breasts, tumor 25, immobilization cup assembly 1, body fixture with straps 18, patient support structure 31, locking mechanism (30 and 31), and the source of radiation 28. By using the breast depressor 29, it significantly reduces the dose to the untreated breast and makes the imaging and treatment setup easier.

It should now be apparent that the above-described device and system for breast tissue immobilization is precise, reliable, repeatable, and predictable, and facilitates imaging and therapy with the patient in a prone position, as well as complete reproduction of that positioning geometry when a recurring procedure is needed. Meanwhile, the untreated breast is depressed to minimize unnecessary radiation exposure.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. For example, although the preferred structure of the cup assembly 1 is two-layers, one-layer may work equally well in many cases (the two-layer embodiment is more able to adapt to different volumes of the breast). It is to be understood, therefore, that the invention may be practiced otherwise than as specifically set forth in the appended claims.

What is claimed is:

1. An apparatus for immobilizing a breast and maintaining a precise geometric relationship between the breast, chest wall, and a patient support structure during breast imaging and therapy with patient in a prone position, comprising:
    a breast immobilization cup assembly including a continuous concave perforated inner layer for receiving a human breast, an airtight continuous outer layer fitted outside the inner layer and defining an airspace there between, an annular flange joined peripherally around said outer layer and said inner layer;
    a vacuum inlet passing through said flange into said airspace; and
    a vacuum source in fluid communication with said vacuum inlet.

2. The apparatus for immobilizing a breast according to claim 1, further comprising a plurality of alignment pins spaced radially around said flange and said pins having distal locking mechanisms at one end.

3. The apparatus for immobilizing a breast according to claim 2, wherein said airtight outer layer and inner layer define a plurality of independent vacuum bands to fine-control cup repositioning to the breast.

4. The apparatus for immobilizing a breast according to claim 2, further comprising a skin marking system comprising a structured grid of radial and axial imaging lines on the cup assembly, and wherein said inner layer and said out layer are both substantially transparent.

5. The apparatus for immobilizing a breast according to claim 2, further comprising a stereotactic imaging marker system including a plurality of stripes integral with the cup assembly and formed of a material that is distinguishable from body structure in CT and/or MRI images, said plurality of stripes further comprising at least a radial stripe around the base of the cup assembly and a stripe running point to diametric point overtop the cup assembly.

6. The apparatus for immobilizing a breast according to claim 2, further comprising
    a breast frame having an aperture sized to accept said outer layer and a plurality of holes spaced radially around said aperture for pass-through of said alignment pins; and
    patient body straps
whereby said breast frame and said patient body straps capture said cup assembly against a patient's body.

7. The apparatus for immobilizing a breast according to claim 2, wherein said patient support structure comprises a locking mechanism for locking engagement of said cup assembly thereto, said locking mechanism including a framed aperture for receiving said cup assembly, and a plurality of holes in the frame for insertion of said alignment pins.

8. The apparatus for immobilizing a breast according to claim 2, wherein the breast adheres to said cup assembly inner layer when a negative vacuum is applied by said vacuum source.

9. An apparatus for immobilizing a breast and maintaining a precise geometric relationship between the breast, chest wall, and patient support structure during breast imaging and therapy, comprising:
    a breast immobilization cup assembly including a continuous concave perforated inner layer conforming to a human breast, a continuous outer layer, an airspace between said inner and outer layers, an annular flange joined peripherally around said outer layer and said inner layer, and a vacuum inlet through said flange into said airspace; and
    a vacuum source in fluid communication with said vacuum inlet.

10. The apparatus for immobilizing a breast according to claim 9, wherein said cup assembly inner layer adheres to said breast when a negative vacuum is applied to said airspace by said vacuum source.

11. The apparatus for immobilizing a breast according to claim 10, further comprising a plurality of alignment pins spaced radially around said flange.

12. The apparatus for immobilizing a breast according to claim 11, wherein said plurality of alignment pins have distal locking mechanisms at one end.

13. The apparatus for immobilizing a breast according to claim 12, wherein said patient support structure comprises a locking mechanism for locking engagement of said cup assembly thereto.

14. The apparatus for immobilizing a breast according to claim 13, wherein said locking mechanism includes a framed aperture for receiving said cup assembly, and a plurality of holes in the frame for insertion of said alignment pins.

15. The apparatus for immobilizing a breast according to claim 9, wherein said inner and outer layers are substantially transparent.

16. The apparatus for immobilizing a breast according to claim 15, further comprising a skin marking system comprising a grid of radial and axial imaging lines on the cup assembly.

17. The apparatus for immobilizing a breast according to claim 9, further comprising:
    a breast frame having an aperture sized to accept said outer layer and a plurality of holes spaced radially around said aperture for pass-through of said alignment pins; and
    patient body straps
whereby said breast frame and said body straps support said cup assembly against a patient's body.

18. The apparatus for immobilizing a breast according to claim 17, further comprising a three-dimensional localization system including a first imaging stripe for enhancing an image signal running radially around the base of the cup assembly, and a second imaging stripe for enhancing an image signal running point to diametric point overtop the cup, and said first and second stripes are formed of a material that is distinguishable from a body structure in CT and/or MRI image.

19. A method for immobilizing a breast and maintaining a precise geometric relationship between the breast, chest wall, and a patient support structure during breast imaging and therapy, comprising the steps of:

provided a breast immobilization cup assembly comprising,
- a continuous concave outer layer and a continuous perforated inner layer with an airspace there between conforming to a human breast, and
- an annular flange joined peripherally around said outer layer and said inner layer, having a plurality of alignment pins spaced radially around said flange;

providing a breast frame having an aperture sized to accept said outer layer of the cup assembly, patient body straps, and a plurality of holes for pass-through of said alignment pins;

attaching said breast immobilization cup assembly to said breast frame by aligning said outer layer and said alignment pins with said aperture and said holes of the breast frame, respectively, and bringing said breast frame flush with said annular flange;

applying a negative vacuum to the airspace of said cup assembly;

inserting a patient's breast into said cup assembly;

supporting said cup assembly and said breast frame to a patient's body by securing said patient body straps;

positioning the patient on a support structure having a breast aperture and a plurality of holes for pass-through of said alignment pins by insertion of the cup assembly and alignment pins through said breast aperture and said holes of support structure, respectively, and attachment thereto.

\* \* \* \* \*